US012605712B2

(12) United States Patent
Akbari et al.

(10) Patent No.: US 12,605,712 B2
(45) Date of Patent: Apr. 21, 2026

(54) DROPLET MICROARRAYS

(71) Applicant: Sartorius Stedim Cellca GmbH, Ulm (DE)

(72) Inventors: Samin Akbari, Winchester, MA (US); Christoph Zehe, Ehingen (DE); David Pollard, South Boston, MA (US)

(73) Assignee: Sartorius Stedim Cellca GmbH, Ulm (DE)

( * ) Notice: Subject to any disclaimer, the term of this patent is extended or adjusted under 35 U.S.C. 154(b) by 603 days.

(21) Appl. No.: 18/097,956

(22) Filed: Jan. 17, 2023

(65) Prior Publication Data

US 2023/0149934 A1     May 18, 2023

Related U.S. Application Data

(63) Continuation-in-part of application No. PCT/US2021/042509, filed on Jul. 21, 2021.

(60) Provisional application No. 63/054,851, filed on Jul. 22, 2020.

(51) Int. Cl.
B01L 3/00       (2006.01)
C12M 1/12       (2006.01)

(52) U.S. Cl.
CPC ........... B01L 3/5088 (2013.01); B01L 3/5085 (2013.01); B01L 3/50853 (2013.01); C12M 25/01 (2013.01); *B01L 2200/10* (2013.01); *B01L 2200/142* (2013.01); *B01L 2300/0819* (2013.01); *B01L 2300/0848* (2013.01); *B01L 2300/12* (2013.01); *B01L 2300/161* (2013.01); *B01L 2300/165* (2013.01)

(58) Field of Classification Search
CPC .. B01L 3/5088; B01L 3/5085; B01L 3/50853; B01L 2200/10; B01L 2200/142; B01L 2300/0819; B01L 2300/0848; B01L 2300/12; B01L 2300/161; B01L 2300/165; C12M 25/01
See application file for complete search history.

(56) References Cited

U.S. PATENT DOCUMENTS

| 6,565,813 B1 * | 5/2003 | Garyantes ........... B01L 3/50853 |
| | | 435/288.3 |
| 9,581,527 B2 | 2/2017 | Leck et al. |
| 2004/0018615 A1 | 1/2004 | Garyantes |
| 2017/0307486 A1 | 10/2017 | Leck et al. |
| 2018/0311671 A1 | 11/2018 | Cook et al. |
| 2020/0199649 A1 | 6/2020 | Reichen et al. |
| 2021/0023562 A1 * | 1/2021 | Mao .................. B01L 3/502792 |

(Continued)

FOREIGN PATENT DOCUMENTS

| CN | 111521662 A * | 8/2020 | ......... G01N 27/4145 |
| EP | 2 684 601 A1 | 1/2014 | |
| EP | 2102650 B1 | 5/2021 | |

(Continued)

OTHER PUBLICATIONS

JP-2006266974-A, English Translation (Year: 2006).*

(Continued)

*Primary Examiner* — Ryan D Walsh

(74) *Attorney, Agent, or Firm* — Wolf, Greenfield & Sacks, P.C.

(57)     ABSTRACT

Methods for forming arrays of droplets, and associated arrays of droplets, are generally provided.

20 Claims, 14 Drawing Sheets

(56)                  References Cited

U.S. PATENT DOCUMENTS

2021/0149184 A1 *    5/2021    Zhitomirsky ..... B01L 3/502792

FOREIGN PATENT DOCUMENTS

JP          2006266974 A   * 10/2006
WO      WO-2012061308 A1 *    5/2012    .......... B01L 3/50853
WO      WO 2015/061362 A1      4/2015

OTHER PUBLICATIONS

CN-111521662-A, English Translation (Year: 2020).*
WO-2012061308-A1, English Translation (Year: 2012).*
Chatzimichail et al., Counting Proteins in Single Cells with Addressable Droplet Microarrays. J Vis Exp. Jul. 6, 2018;(137):56110. doi: 10.3791/56110.
Feng et al., Droplet Microarrays: From Surface Patterning to High-Throughput Applications. Adv Mater. May 2018;30(20):e1706111. doi: 10.1002/adma.201706111. Epub Mar. 23, 2018.
Su et al., A miniature droplet reactor built on nanoparticle-derived superhydrophobic pedestals. Nano Res. Dec. 17, 2010;4(3):266-73.
International Search Report and Written Opinion for International Application No. PCT/US2021/042509 date Nov. 4, 2021.
International Preliminary Report on Patentability (Chapter 1) for International Application No. PCT/US2021/042509 dated Feb. 2, 2023.
Kim et al., The role of surface energy in heterogeneous bubble growth on ideal surface. Int J Heat Mass Transfer. May 2017;108(Part B):1901-9.

* cited by examiner

104

404

304

$h_w$          $h_d$

204

104

404

304

$h_w$          $h_d$

204

504

604

704

204

504

604

504

204

504

504

DROPLET MICROARRAYS

RELATED APPLICATIONS

This application is a continuation-in-part of International Application No. PCT/US21/42509, filed Jul. 21, 2021, and entitled "Droplet Microarrays", which claims priority to U.S. Provisional Application No. 63/054,851, filed Jul. 22, 2020, and entitled "Droplet Microarrays", both of which are incorporated herein by reference in their entireties for all purposes.

FIELD

Arrays of droplets and methods for forming arrays of droplets are generally provided.

BACKGROUND

Many techniques for performing analyses on fluid samples require substrates that topologically confine the fluid samples. Such substrates may require appreciable effort to manufacture and/or may be challenging to reconfigure when experimental needs change.

Accordingly, new substrates suitable for supporting arrays of droplets and associated methods are needed.

SUMMARY

The present disclosure generally describes droplet arrays. The subject matter described herein involves, in some cases, interrelated products, alternative solutions to a particular problem, and/or a plurality of different uses of one or more systems and/or articles.

In some embodiments, a method of forming an array of droplets is provided. The method comprises depositing a plurality of droplets onto a surface and enclosing some or all of the droplets in the plurality of droplets in an enclosure. The surface is flat. The surface has a uniform surface chemistry. The surface is hydrophobic. The plurality of droplets comprises greater than or equal to 10 droplets. The enclosure reduces and/or prevents the evaporation of water from the droplets.

In some embodiments, an array of droplets is provided. The array of droplets comprises a plurality of droplets disposed on a surface. The surface is flat. The surface has a uniform surface chemistry. The surface is hydrophobic. The plurality of droplets comprises greater than or equal to 10 droplets. Some or all of the droplets in the plurality of droplets are enclosed by an enclosure. The enclosure reduces and/or prevents evaporation of water from the droplets.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIGS. 4-5A, and 5B show schematic depictions of an array of droplets positioned inside an enclosure, in accordance with some embodiments;

DETAILED DESCRIPTION

Figure 1:
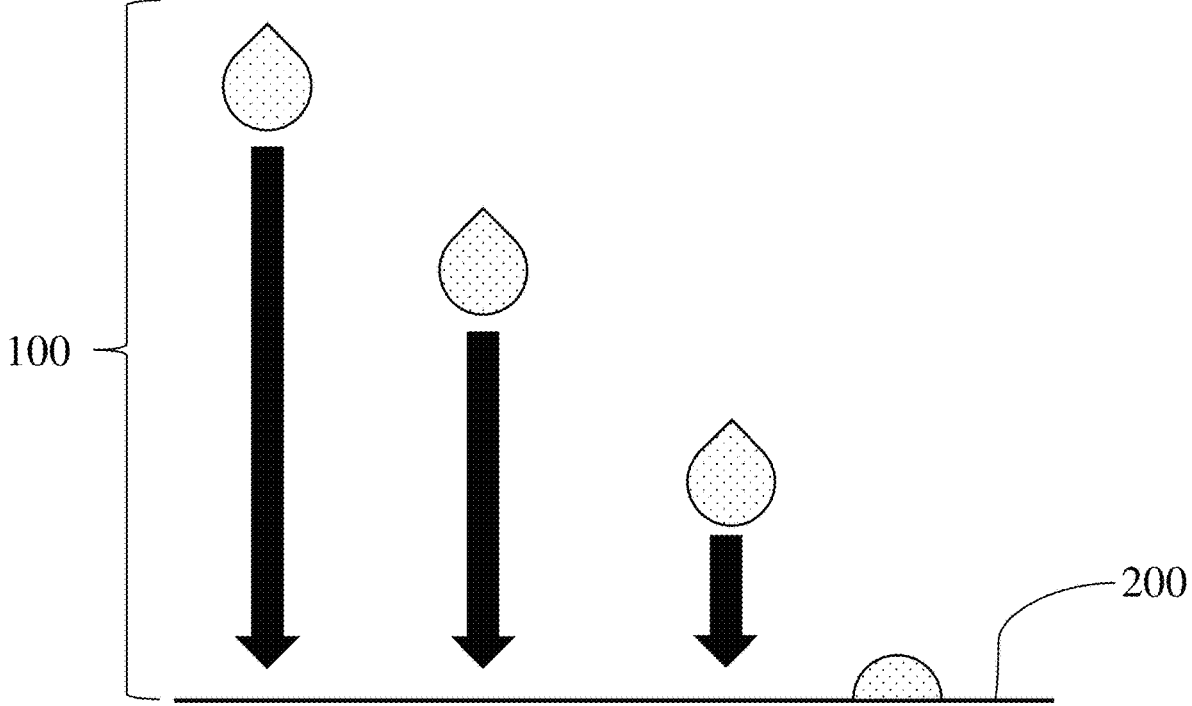
FIG. 1 shows a schematic depiction of a method of depositing a plurality of droplets onto a surface, in accordance with some embodiments.

Methods for forming arrays of droplets, and associated arrays of droplets, are generally provided.

Some methods for forming arrays of droplets described herein relate to the formation of droplets on substrates that require minimal or no preparation prior to the formation of the array of droplets. Arrays of droplets positioned on such substrates are also described. Such substrates may be easy to acquire and/or rapidly prepare for the formation of arrays of droplets. Accordingly, such substrates may advantageously provide the ability to form substrates suitable for supporting arrays of droplets quickly and/or in response to research and/or testing needs (e.g., to perform an initial and/or small-scale pilot study, to scale up successful experiments). As described in further detail below, some such substrates may comprise a hydrophobic, flat surface that has uniform surface chemistry and may support an array of droplets.

Some methods for forming arrays of droplets relate to the formation of droplets on substrates that are suitable for supporting arrays of droplets having a variety of different designs (e.g., arrays of droplets having different droplet sizes, spacings, and the like). Such substrates may be particularly suitable for forming arrays of droplets in research and/or testing environments. For instance, in some research and/or testing environments, arrays of droplets having different features are continually designed for investigating different droplet properties and/or different features of species contained within the droplets. As another example, in some research and/or testing environments, arrays of different types of droplets are continually designed for investigating the properties of droplets having different sizes, shapes, and/or chemical compositions. For such research and/or testing environments, substrates that can support a variety of types of arrays of droplets are desirable and/or may facilitate rapid (and/or rapidly-changing) research and/or testing projects.

One feature that is present in some substrates described herein that may be beneficial for supporting arrays of droplets having different designs is the presence of a flat surface. As such, in some embodiments, flat surfaces described herein lack one or more topological features that would confine a droplet and/or affect the positional stability of a droplet disposed thereon. By contrast, substrates that lack a flat surface (e.g., that have surfaces comprising one or more topological features on a length scale that would confine a droplet and/or affect the positional stability of a droplet disposed thereon) may comprise some portions to which droplets may be confined. As one example, for substrates comprising pluralities of wells, droplets positioned in the wells may be confined to the wells unless the substrate is tipped and/or the droplets are aspirated from the wells. Additionally, droplets deposited on the sides of wells and/or on raised portions of the substrate positioned between the wells may flow under the influence of gravity into wells. Practically, this means that it may be challenging or impossible to use such substrates to support arrays of droplets in which the droplets are positioned in locations other than the wells and/or in which the droplets have volumes in excess of the wells. Substrates that lack flat surfaces but do not comprise wells may also show similar drawbacks, as topological features thereon may cause droplets to flow and/or be pinned at certain locations.

By contrast, flat surfaces may provide a surface that includes no topological features that would confine and/or affect the positional stability of droplets and/or may comprise no such features in the location(s) in which droplets are positioned. The flatness of the surface may cause each location on the substrate to be equally stable for a droplet from a topological perspective. This may allow for droplets to be positioned in arrays that comprise droplets of different sizes and/or spacings that are equally, or close to equally, stable.

It should be noted that some surfaces may comprise a portion that is flat, and on which the array of droplets are positioned, and further comprise one or more topological features on a length scale that would confine a droplet and/or affect the positional stability of a droplet disposed thereon. For instance, some surfaces may be flat, and may comprise droplets positioned thereon, but may further comprise a depression and/or handle along the edge. In some embodiments, droplets in an array of droplets are positioned on a common portion of a surface that does not comprise any topological features that assist with keeping the droplets separated from each other, they may be considered to be positioned on a flat surface even if the surface further comprises topological features.

Another feature that is present in some substrates described herein that may be beneficial for supporting arrays of droplets having different designs is uniform surface chemistry. Substrates that have spatially-varying surface chemistries (e.g., that comprise one or more variations in chemistry on a length scale that would confine a droplet and/or affect the positional stability of a droplet disposed thereon) may comprise some portions that comparatively promote droplet spreading (e.g., portions with higher surface tension) and some portions that comparatively inhibit droplet spreading (e.g., portions with lower surface tension). Droplets positioned on such surfaces may be caused to flow towards the portions that promote droplet spreading and/or away from portions that inhibit droplet spreading. For this reason, it may be challenging to form arrays of droplets that are positioned in locations other than those that promote droplet spreading and/or that have volumes in excess of the volume that can be stably positioned on the portions that promote droplet spreading.

On the other hand, substrates that have a uniform surface chemistry and/or have a uniform surface chemistry in the location(s) in which the droplets are positioned may present a surface for droplet deposition in which each location interacts with the droplets in a manner that is chemically very similar or identical. Droplets deposited on such surfaces may be equally, or close to equally, likely to spread at any location of the surface. This, too, may allow for droplets to be positioned in arrays that comprise droplets of different sizes and/or spacings that are equally, or close to equally, stable.

It should be noted that some surfaces may comprise a portion that has a uniform surface chemistry, and on which the array of droplets are positioned, and further comprise variations in chemistry on a length scale that would confine a droplet and/or affect the positional stability of a droplet disposed thereon. For instance, some surfaces may have a uniform surface chemistry, and comprise droplets positioned thereon, but further comprise a region along the edge which has a differing surface chemistry. In some embodiments, droplets in an array of droplets are positioned on a common portion of a surface that comprise any variations in chemistry that assist with keeping the droplets separated from each other, they may be considered to be positioned on a surface having a uniform surface chemistry even if the surface further comprises other variations in chemistry.

A third feature that is present in some substrates described herein that may be beneficial for supporting arrays of droplets having different designs is the presence of a hydrophobic surface. Without wishing to be bound by any particular theory, it is believed that droplets are likely to spread on surfaces that they have a lower surface tension than and to form larger contact angles on surfaces that they have a higher surface tension than. Accordingly, surfaces that have relatively low high surface tensions, such as hydrophilic surfaces, may cause droplets thereon to spread. Such spreading may undesirably bring droplets that are initially separated from each other, and that are designed to be maintained separate from each other, into contact. Surfaces that have relatively high surface tensions, such as hydrophobic surfaces, may cause droplets to ball up. If not caused to flow (e.g., under the influence of a force), such droplets may be advantageously maintained separate from each other.

Figure 2:
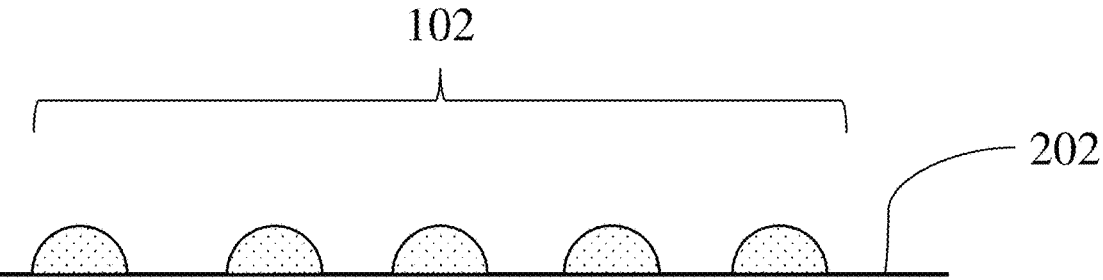
FIGS. 2-3 show schematic depictions of an array of droplets, in accordance with some embodiments.
Figure 3:
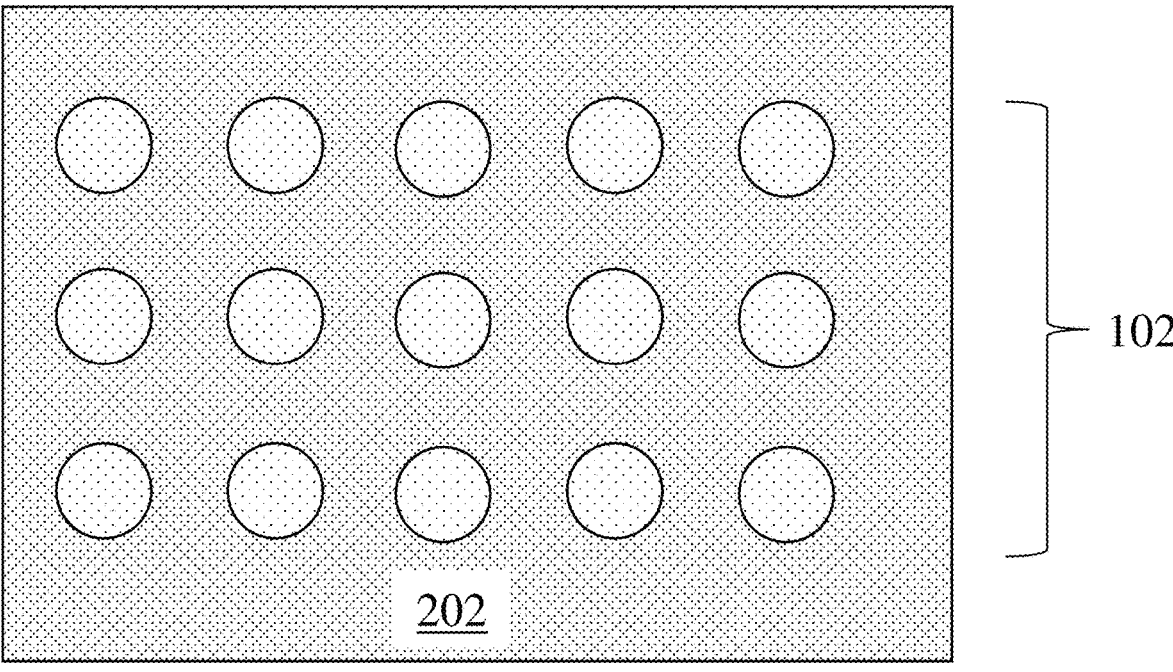

As described elsewhere herein, some methods comprise depositing a plurality of droplets onto a surface. FIG. 1 shows one non-limiting embodiment of a method for doing so. In FIG. 1, a plurality of droplets 100 is deposited onto a surface 200. FIG. 2 shows a side view of one non-limiting embodiment of an array of droplets (e.g., an array of droplets formed by the procedure depicted in FIG. 1). FIG. 3 shows a top view of this same array of droplets. In FIGS. 2 and 3, the plurality of droplets 102 is disposed on the surface 202.

In some embodiments, an array of droplets may have one or more features similar to the features shown in FIGS. 2 and 3. For instance, in some embodiments, an array of droplets comprises droplets that have a relatively uniform volume, a relatively uniform spacing, and/or are positioned in a lattice formation (e.g., a square lattice). It is also possible for arrays of droplets to differ from those shown in FIGS. 2 and 3 in one or more ways. For instance, some arrays of droplets may comprise droplets of varying volume, varying spacing, and/or that are not positioned in a lattice formation (e.g., that are positioned randomly). Further details regarding various features of arrays of droplets are provided in further detail below.

Similarly, some methods for depositing arrays of droplets may have some features in common with the method shown in FIG. 1 and some methods for depositing arrays of droplets may differ from the method shown in FIG. 1 in one or more ways. By way of example, as shown in FIG. 1, droplets may change shape (e.g., through spreading, through evaporation, etc.) during and/or after the deposition process. For instance, droplets may have a spherical shape at one or more points in time prior to contacting a surface and then have a spherical cap shape after contacting the surface. As another example, droplets may be deposited sequentially, simultaneously, or both sequentially and simultaneously. For instance, a first set of droplets may be deposited simultaneously, a second set of droplets may then be deposited simultaneously, etc. Simultaneous deposition of droplets may be accomplished through the use of a component comprising multiple nozzles that can deposit droplets simultaneously (e.g., a multi-nozzle injector). It should also be noted that some methods of depositing droplets may comprise further steps and/or may make use of further components not shown in FIG. 1 (e.g., in some embodiments, droplets are deposited from a nozzle and/or a component comprising multiple nozzles).

Droplet deposition may be performed in a variety of suitable manners. In some embodiments, droplets are deposited manually (e.g., by pipette). In some embodiments, droplets are deposited with the assistance of one or more instruments. As an example, a droplet dispensing system is employed to deposit droplets in some embodiments. The droplet dispensing system may comprise a source of droplets (e.g., a fluid which may be formed into droplets), a pump (e.g., a piezoelectric pump), and a nozzle. The pump may be configured to pump the fluid and/or the droplets through the nozzle, from which they may be expelled and then deposited onto a surface. The nozzle may expel the droplets directly into air, or may expel the droplets into a fluid other than air (e.g., an oil). In some embodiments, the nozzle expels the droplets into the fluid other than air, and then expels droplets encapsulated in that fluid into air. It is also possible for a droplet dispensing system to further comprise one or more motors configured to translate the nozzle to different locations above a surface onto which the droplets are being deposited and/or to further comprise one or more motors to translate a substrate comprising the surface to different locations beneath the nozzle depositing the droplets.

Some suitable droplet deposition systems may be microfluidic and/or comprise microfluidic components. Such microfluidic components may include microfluidic channels, and/or nozzles.

When employed, droplet dispensing systems may operate fully autonomously (i.e., with no user input), may solicit input from users at one or more points in time, and/or may be configured to respond to user inputs. For instance, a droplet dispensing system may be configured to start and/or stop dispensing droplets in response to user input. In some embodiments, a droplet dispensing system may dispense (or fail to dispense) each droplet in response to user input.

In some embodiments, a droplet dispensing system comprises a component configured to interrogate the droplets prior to deposition (e.g., after droplet formation but prior to droplet deposition) and/or to interrogate one or more precursors to the droplets prior to droplet formation. For instance, a droplet dispensing system may comprise a component that is configured to interrogate a fluid from which one or more droplets may be formed (e.g., a fluid positioned in a channel). The interrogation may be performed optically (e.g., by use of an optical microscope, a camera, and/or a light source) and/or in any other suitable manner. When performed, the interrogation may comprise determining one or more properties of the droplet. Such properties may include volume, contents (e.g., whether or not the droplet comprises a cell and/or a bead), chemical composition, etc. In some embodiments, a droplet dispensing system may interrogate a droplet, and, based on the results of the interrogation, determine whether or not to dispense the droplet. As an example, in some embodiments, a droplet dispensing system may interrogate a droplet to determine whether or not it comprises a species of interest (e.g., a cell), possibly in an amount of interest (e.g., comprising a single cell), and then dispense the droplet only if it comprises the species of interest and/or comprises that species in the amount of interest. Droplets lacking the species of interest (and/or comprising the species of interest in an undesired amount) may instead be disposed of. Some or all of these processes may be performed automatically (e.g., without user input). Additionally, in some embodiments, a droplet dispensing system is configured to interrogate a droplet and then transmit information determined by the interrogation to a user. The user may then direct the droplet dispensing system to either dispense the droplet or to dispose of the droplet.

After formation of an array of droplets, one or more further steps may be performed. The further step(s) may be performed while the droplets are positioned in the array, or after removal of one or more of the droplets from the array.

Figure 4:
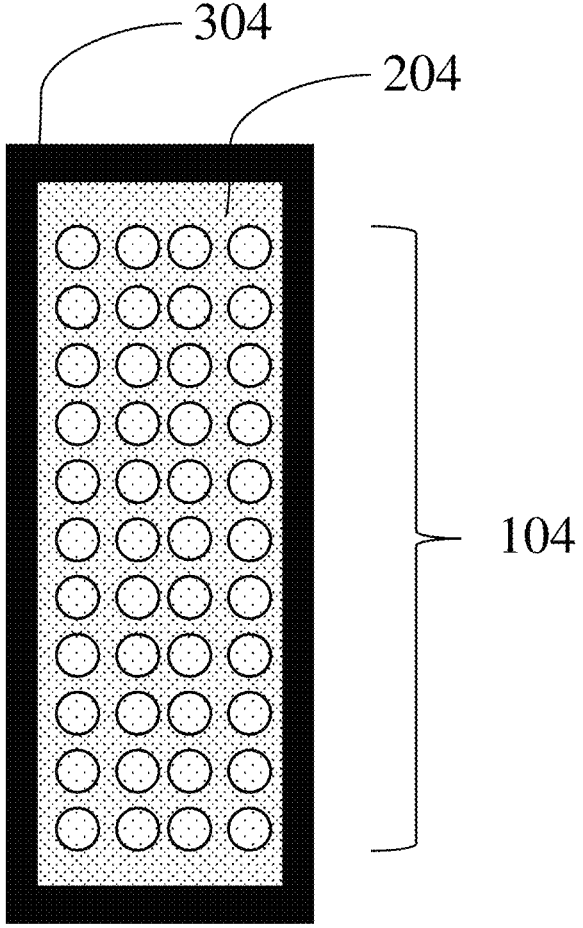
Figure 5A:
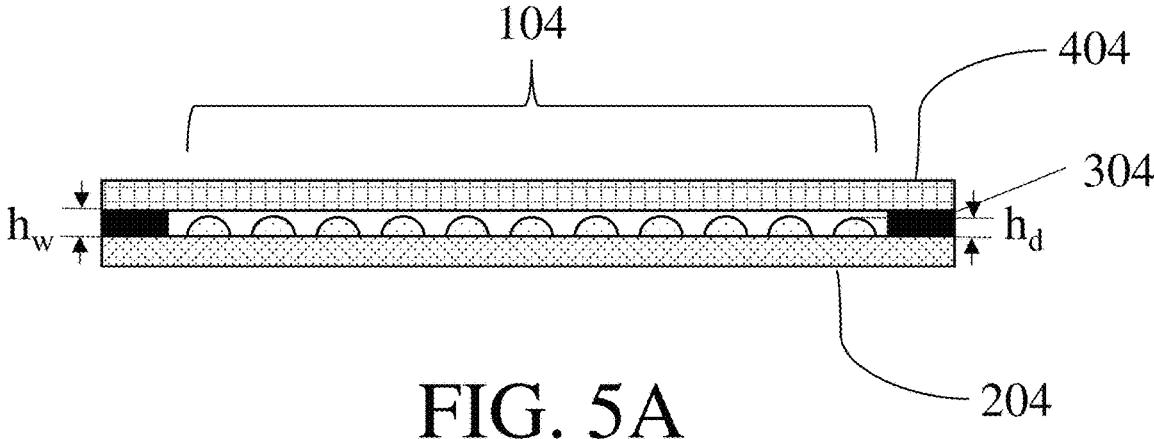
Figure 5B:
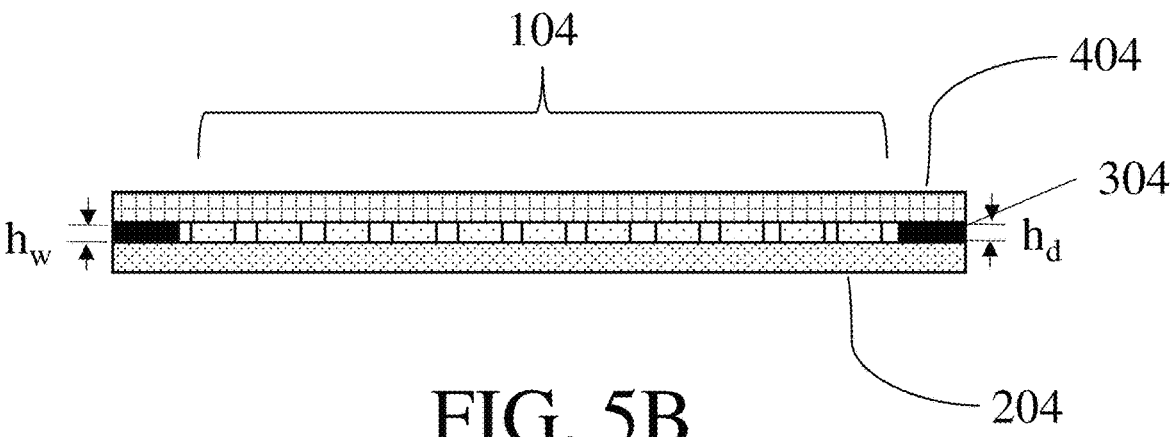
Figures 6, 7:
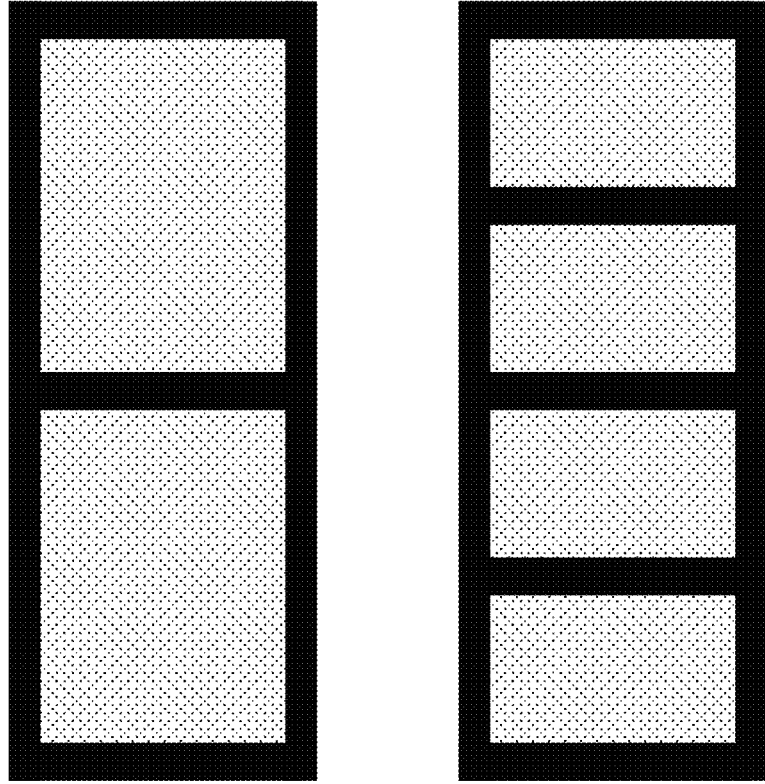
FIGS. 6-12 show schematic depictions of enclosure designs, in accordance with some embodiments.
Figure 8:
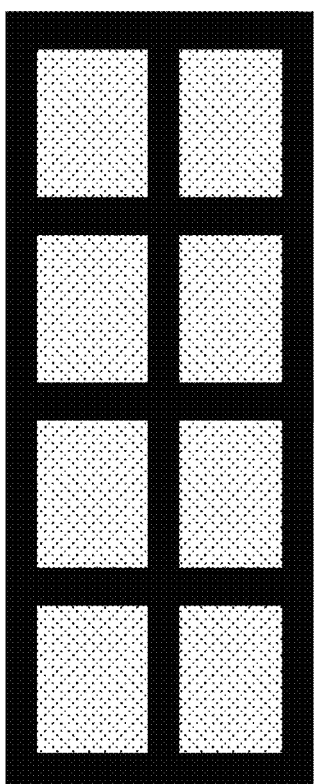
Figure 9:
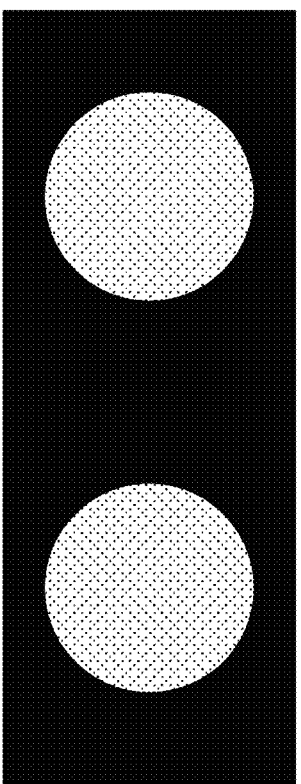
Figure 10:
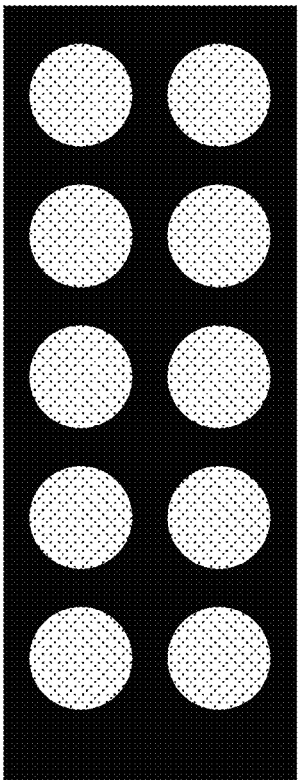
Figure 11:
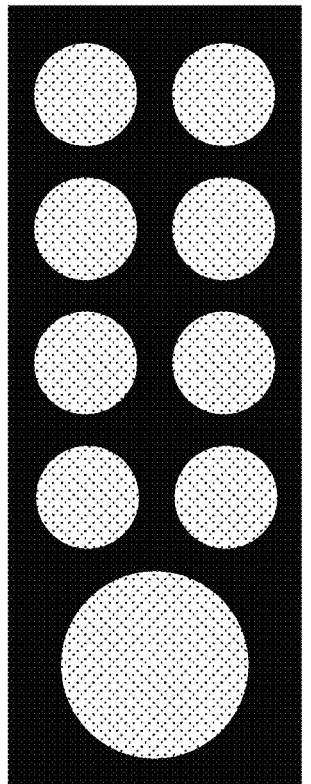
Figure 12:
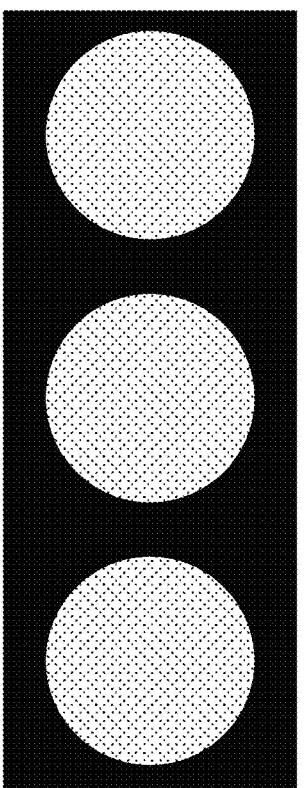

One example of a further step that may be performed while the droplets are positioned in the array is the formation of an enclosure that surrounds some or all of the droplets in the array. The enclosure may surround the droplets (e.g., on all sides, or some of the sides of the droplets) and/or may be relatively impermeable to liquid and/or gaseous water. Enclosures having both of these features may reduce and/or prevent evaporation of water from the droplets. Advantageously, this property may allow for arrays of droplets to be stored for appreciable periods of time without undergoing a degree of evaporation that would undesirably affect droplet volume and/or water concentration. It is also noted that, in some embodiments, an enclosure is relatively impermeable to liquid water but has appreciable permeability to gaseous water. FIG. 4 shows one example of a top view of an array of droplets positioned inside an enclosure. In FIG. 4, the array of droplets 104 is positioned on a surface 204. The array of droplets is further enclosed by a plurality of side walls 304 and a top surface (not shown). FIGS. 5A and 5B show a side view of the array of droplets shown in FIG. 4. In FIGS. 5A and 5B, the top wall or surface 404 is also shown and wherein the bottom surface is at least partially enclosed by the top wall or surface. In FIG. 5A, the droplets do not contact the top wall or surface, whereas in FIG. 5B, at least a portion (e.g., a top portion) of the droplets are in contact with the top wall or surface. The spacing between the top and bottom walls can be controlled by controlling the height of the side walls and/or the size of the droplets. In some embodiments, the height of the droplet, $h_d$, may be equal to 100% of the height between the top and bottom walls, $h_w$, such that at least a portion of the droplet is in contact with the top wall or surface. In other embodiments, the height of the droplet may be less than 100%, less than or equal to 80%, less than or equal to less than or equal to 40%, or less than or equal to 20% of the height between the top and bottom walls. In some embodiments, the height of the droplet may be at least 10%, at least 30%, at least 50%, at least 70%, or at least 90% of the height between the top and bottom walls. Combinations of the above-referenced ranges are also possible. When a plurality of droplets is present, each of the droplets may have a height in one or more of the above-referenced ranges. In some embodiments, for each of the plurality of droplets, at least a portion of droplet is in contact with the top surface.

As indicated in FIG. 4, the top wall or surface may be formed from a different material than the surface and/or the side walls. However, in other embodiments, the top wall or surface may be formed from the same material as the surface (e.g., bottom surface) and/or from the same material as the side walls. For instance, in some embodiments, the surface (e.g., bottom surface) is the surface of a glass slide or a coating (e.g., a hydrophobic coating as described herein) disposed on a glass slide and the top wall or surface is formed from and/or comprises a glass slide, and may optionally have the same coating (e.g., hydrophobic coating) facing the droplets as that on the surface of the bottom glass slide. In yet other embodiments, the materials used to form the top and bottom walls may be different (or the same), but the walls may have a same or similar coating on the surface portion that comes into contact with the droplets. Accordingly, the tops and bottoms of the droplets may be exposed to or in contact with the same surface chemistry at the top and bottom surfaces. In some embodiments, the bottom surface and/or the top surface are hydrophobic.

It should also be noted that, although FIGS. 4, 5A and 5B show side walls that are uniform across their height, it is possible for an enclosure to comprise side walls that have a spatially-varying chemistry and/or structure. As one example, in some embodiments, one portion of a side wall is adhered to the surface supporting the droplets and/or to the top wall or surface by an adhesive (e.g., a silicone adhesive). The adhesive itself may make up a portion of the side wall. In some embodiments, a fixture may be screwed around the enclosure (temporarily or permanently) to compress the enclosure and assist with gasket sealing. It is also possible for side walls to be joined to the surface supporting the droplets and/or to the top wall or surface by screws. The screws themselves may make up portions of the side wall. It is also possible for one or more portion(s) of the side wall to be formed from gaskets, such as silicone gaskets.

When present, an enclosure may surround some or all of the droplets disposed on a surface. It is also possible for two or more enclosures to enclose two or more different portions of an array of droplets disposed on a surface. In some embodiments, the different enclosures may be employed to enclose different types of droplets and/or different environments in which droplets are positioned. Such designs may allow for different types of experiments to be facilely performed on droplets positioned on a common surface and/or for different droplets positioned on a common surface to be exposed to different conditions. For instance, one portion of an array of droplets may be surrounded by an enclosure that encloses a sterile volume and another portion of the array may be surrounded by an enclosure that encloses a volume that is not sterile. In some embodiments, enclosing different droplets in different enclosures may reduce or prevent contamination and/or cross-talk between the droplets in the different enclosures. FIGS. 6-12 show further examples of geometries that enclosures may have. It is also possible for two or more enclosures to enclose the same types of droplets.

Enclosures surrounding droplets may have a variety of suitable shapes and sizes. For instance, enclosures may have circular cross-sections or rectangular (e.g., square) cross-sections. In some embodiments, droplets in an array are enclosed by enclosures of the same shape and/or volume. In some embodiments, some droplets in an array are enclosed by an enclosure having a different shape and/or volume from an enclosure enclosing other droplets in the array. In some embodiments, one or more enclosures has a shape compatible with other laboratory equipment and/or a plurality of enclosures are arranged to have a shape compatible with other laboratory equipment. As one example, a plurality of enclosures may have a geometry that mimics that of a 96 well plate.

As shown illustratively in FIG. 5A, the top wall or surface is not in physical contact with the droplets; however, in other embodiments such as in the configuration shown in FIG. 5B, the top wall or surface is in physical contact with one or more droplets of the array.

In some embodiments, a substrate having a surface on which droplets are disposed further comprises a water reservoir. The water reservoir may be a location in which water can be positioned. Without wishing to be bound by any particular theory, the presence of a water reservoir may advantageously enhance the humidity in the vicinity of the droplets, which may reduce and/or prevent evaporation. This may be particularly desirable when the droplets are employed to perform assays that can take extended periods of time (e.g., more than 12 hours, days, up to two weeks) and/or under heated conditions (e.g., in an incubator, at a temperature of approximately 37° C., at a temperature of up to 40° C., at a temperature of up to 50° C.).

Figure 13:
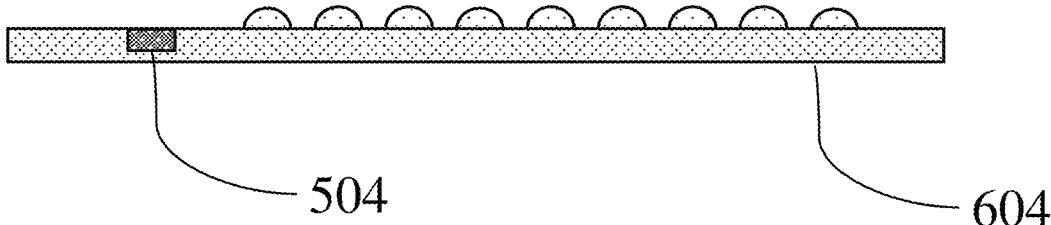
FIGS. 13-17 show schematic depictions of water reservoir designs.

In some embodiments, a water reservoir takes the form of a depression in the substrate. For instance, it may take the form of a groove or well positioned in the substrate. One example of a water reservoir having this design is shown in FIG. 13, in which the water reservoir takes the form of a depression 504 in the substrate 604.

Figure 14:
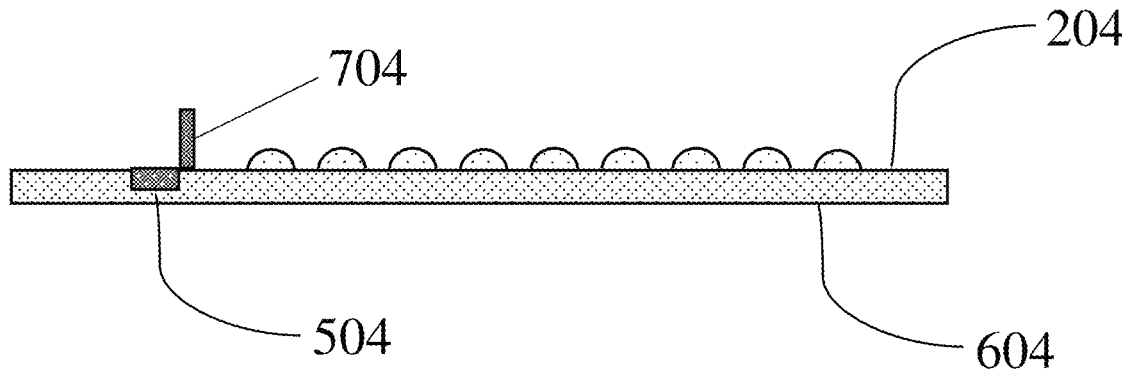

It is also possible for a water reservoir to be separated from one or more other portions of the substrate (e.g., a surface on which droplets are disposed) by a feature that reduces and/or prevents spreading of water from the water reservoir. One non-limiting example of such a feature is a raised ridge. A substrate may comprise both a water reservoir taking the form of a depression in a substrate and a feature that reduces and/or prevents spreading of water from the water reservoir, may comprise the former without the latter, or may comprise the latter without the former. FIG. 14 shows one non-limiting example of a substrate in which a raised ridge 704 separates a water reservoir 504 taking the form of a depression in the substrate 604 from the surface 204. In some embodiments, a raised ridge may surround a water reservoir on all sides or on multiple sizes (e.g., two opposing sides, all sides except one). When both one or more raised ridges and an enclosure comprising a top surface are present, the raised ridge(s) may extend such that they contact the top surface or may extend through only a portion of the height enclosed by the top and bottom walls of the enclosure.

Figure 15:
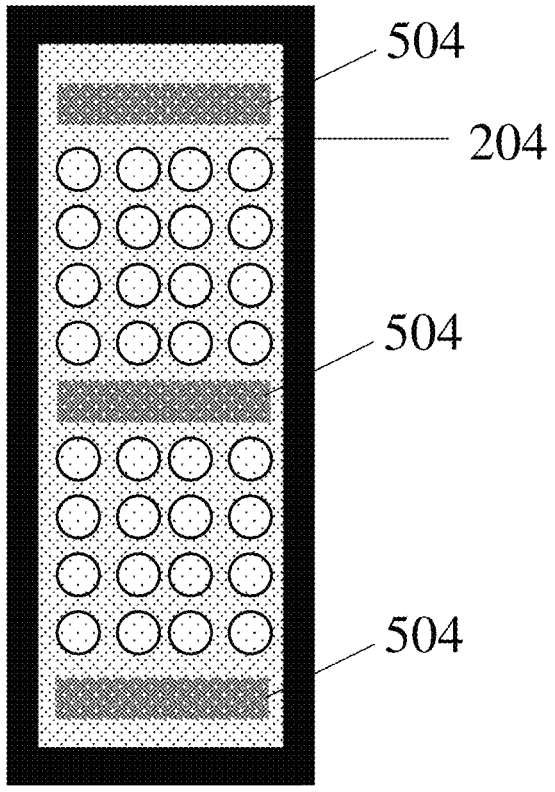
Figure 16:
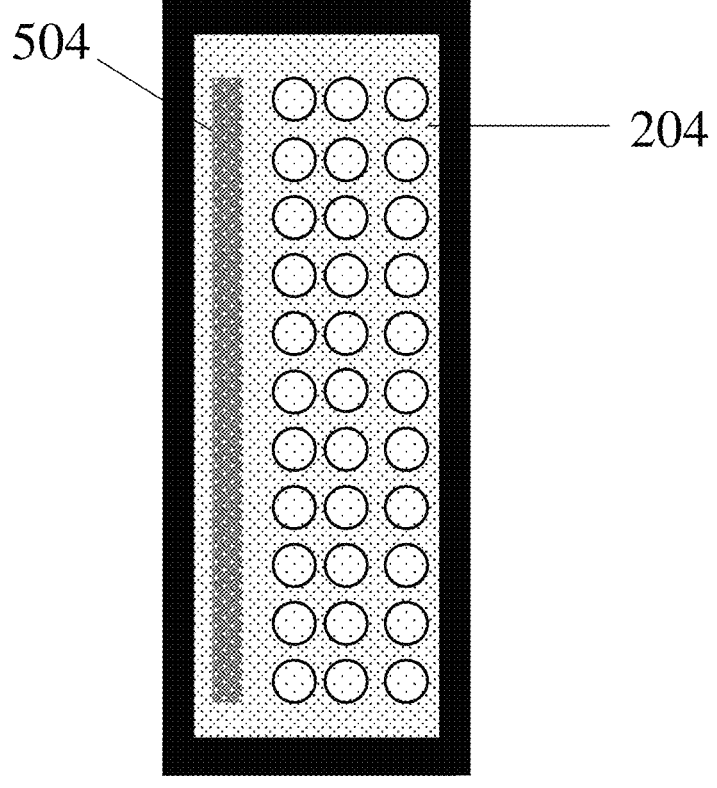
Figure 17:
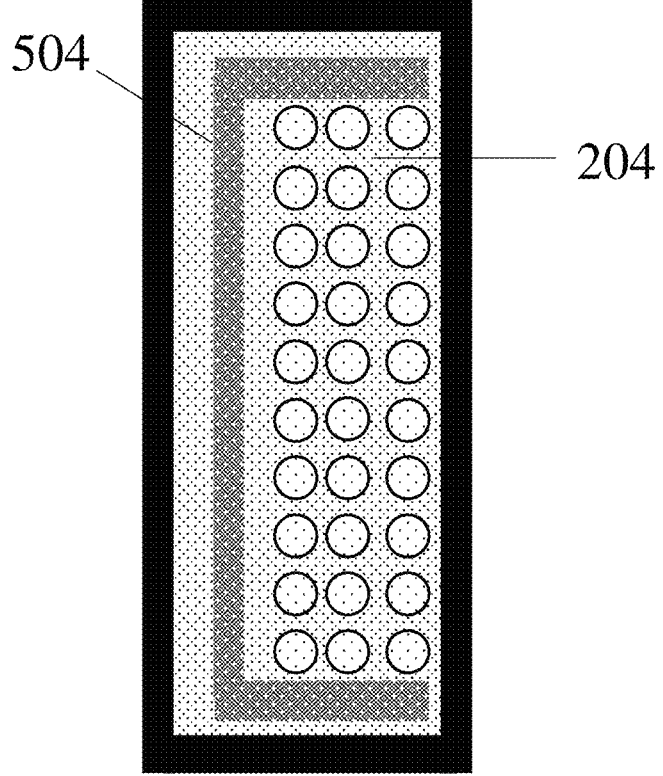

Water reservoirs may have a variety of suitable designs. FIGS. 15-17 show three non-limiting examples of such designs. As shown illustratively in these figures, one or more water reservoirs may be positioned in a single substrate. Such water reservoirs may be separated from one or more other portions of the substrate by raised ridges (not shown). In some embodiments, like the embodiments shown in FIGS. 15-17, the water reservoir(s) may have rectangular shapes and/or may comprise multiple linked rectangles; however, other shapes may also be possible. The water reservoir(s) may be positioned in an interior portion of the substrate (e.g., surrounded by a surface on which droplets are disposed) and/or may be positioned between some or all of the droplets disposed on a surface and a side wall of an enclosure. In some embodiments, one or more water reservoir(s) may form a perimeter around a surface on which droplets are disposed. This perimeter may enclose all of the droplets on the substrate or may be enclosed on one or more (or all sides) by a surface on which droplets are disposed. Similarly, the perimeter may surround all sides of a surface on which droplets are disposed, some of the sides, and/or portions of one or more sides.

In some embodiments, water is positioned inside a water reservoir. The water may be ultrapure water and/or double-distilled water. Without wishing to be bound by any particular theory, it is believed that such water may leave no residue or minimal residue in the water reservoir upon removal therefrom, which may make the substrate easier to clean and/or reuse. In some embodiments, a further step comprises removal of one or more of the droplets from the array (e.g., prior to performing one of the further steps described elsewhere herein, after performing one of the further steps described elsewhere herein). Droplet removal may be performed manually (e.g., by pipetting) or in an automated manner (e.g., by use of a robotic arm).

In some embodiments, cells are grown in some or all of the droplets in the array; optionally, as a function of time. Growing cells in the droplets may comprise incubating the droplets for a period of time (e.g., several hours, several days, one or more weeks). The cell growth and/or clonal formation may be monitored (e.g., by microscopy), optionally in real time. In some embodiments, droplets in which an appreciable amount of cell growth is observed may be identified and/or removed from the array. Such droplets may then be placed in a suitable environment to promote even further growth and/or expansion. It is also possible for droplets in which limited or no cell growth is observed to be discarded (e.g., by removing them from the array of droplets, by discarding an array of droplets after droplets in which an appreciable amount of cell growth have been removed from the array of droplets and then discarding the array of droplets).

It is also possible for other features of the droplets to be monitored as a function of time. As one example, in some embodiments, crystal growth of proteins in one or more of the droplets is monitored as a function of time (e.g., in real time).

In some embodiments, one or more experiments and/or testing are performed on some or all of the droplets in the array. For instance, in some embodiments, an assay (e.g., a single cell assay, an ELISA assay, an immunoassay) is performed on the contents of some or all of the droplets in the array. As another example, in some embodiments, a FRET-based assay is performed on the contents of some or all of the droplets in the array. The FRET-based assay may provide information regarding the titer of protein secreted by any cells present in the droplets. Performance of an assay and/or FRET may comprise observing the fluorescence of the droplets (e.g., in a fluorescent microscope).

In some embodiments, the performance of experiments in droplets (e.g., the droplets in the arrays described herein) may be relatively rapid and/or may allow for relatively high throughput in comparison to the performance of such experiments in types of fluids (e.g., bulk fluids, larger aliquots of fluids). For instance, in some embodiments, a method may comprise producing and/or depositing droplets at rates of up to several kHz. In some embodiments, the performance of experiments in droplets (e.g., the droplets in the arrays described herein) may make use of relatively small amounts of reagents (e.g., pL to nL volumes of reagents) in comparison to the performance of such experiments in types of fluids. These features may advantageously reduce the cost of performing the experiments.

As described elsewhere herein, some embodiments relate to arrays of droplets and methods by which such arrays may be formed. Further features of the arrays of droplets are provided below.

The arrays of droplets may comprise droplets positioned with respect to each other in a variety of suitable manners.

As described above, in some embodiments, the droplets are positioned in a lattice formation. Lattices having a variety of suitable symmetries are possible. For instance, square lattices, rectangular lattices, and hexagonal lattices are possible. When droplets are positioned in a lattice formation, they may be positioned exactly on the lattice points or may deviate from the lattice points to a small degree. For instance, in some embodiments, droplets are positioned in a lattice formation such that the standard deviation of the distance from the lattice point is less than or equal to 20%, less than or equal to 15%, less than or equal to 10%, less than or equal to 7.5%, less than or equal to 5%, less than or equal to 2%, or less than or equal to 1% of the distance between the lattice points.

The droplets in an array may have a variety of suitable compositions. In some embodiments, an array comprises droplets that are suitable for performing biological processes and/or are biocompatible. For instance, in some embodiments, an array comprises droplets that are sterile. As further examples, an array may comprise droplets that have a pH and/or salinity that are non-toxic. In some embodiments, an array comprises droplets that are non-toxic and/or that lack toxic components.

In some embodiments, droplets in an array comprise water. Such droplets may further comprise one or more additional species soluble in water (e.g., the droplets may comprise an aqueous solution) and/or suspendable in water (e.g., the droplets may comprise an aqueous suspension). As an example, in some embodiments, droplets in an array comprise an aqueous buffer. The aqueous buffer may be any physiological buffer, non-limiting examples of which include phosphate-buffered saline, tris-based buffers, and HEPES-based buffers. As another example, droplets in an array may comprise cell culture media. The cell culture media may be an aqueous composition capable of maintaining living cells.

It is also possible for droplets in an array to comprise one or more biological materials, including biological materials that are dissolved and/or suspended in water. For instance, some droplets in an array may comprise cells and/or biologically-relevant molecules, examples of which include, but are not limited to: proteins, DNA, and/or RNA. When the droplets in an array comprise cells, they may further comprise one or more species that promote cell growth, non-limiting examples of which include, but are not limited to: cell culture media, cell culture media components, and/or growth factors.

In some embodiments, droplets in an array comprise one or more components suitable for performing a chemical and/or biological reaction. In some embodiments, the reaction may be an assay. The assay may be an assay suitable for determining the effect and/or toxicity of a drug and/or for determining an appropriate dose of a drug. The components suitable for performing the reaction may be reagents. Non-limiting examples of reagents include reagents suitable for performing an assay (e.g., a single-cell assay, an ELISA assay, an immunoassay) and/or reagents suitable for performing FRET-based assays. In some embodiments, all the reagents necessary to perform a particular assay and/or reaction are provided in each droplet. It is also possible for the droplets to both comprise one or more of the reagents necessary to perform a particular assay and/or reaction and lack one or more of the reagents necessary to perform a particular assay and/or reaction. The missing reagents, if any, may be provided prior to performance of the assay (e.g., directly prior to such performance).

In some embodiments, droplets in an array may comprise one or more components suitable for performing a chemical and/or biological reaction that comprises binding. Binding may comprise a reaction between a target and a binding partner that specifically binds to the target (e.g., an agent or molecule that specifically binds to the target). In some embodiments, the binding partner may specifically bind to an epitope on the target molecule. Non-limiting examples of suitable binding partners include proteins, nucleic acids, glycoproteins, carbohydrates, hormones, inorganic compounds, and sequestration compounds. Non-limiting examples of specific pairs of binding partners and targets include an antibody and an antigen, an antibody fragment and an antigen, an antibody and a hapten, an antibody fragment and a hapten, an enzyme and an enzymatic substrate, an enzyme and an inhibitor, an enzyme and a cofactor, a binding protein and a substrate, a carrier protein and a substrate, lecithin and a carbohydrate, a receptor and a hormone, a receptor and an effector, complementary strands of nucleic acid, a protein in combination with a nucleic acid repressor and an inducer, a ligand and a cell surface receptor, and a virus and a ligand.

Non-limiting examples of antibodies that may be binding partners or antibodies include intact (i.e., full-length) polyclonal and monoclonal antibodies, antigen-binding fragments of polyclonal and monoclonal antibodies (such as Fab, Fab', F(ab')2, or Fv), single chains (scFv), mutants of single chains, fusion proteins comprising an antibody portion, humanized antibodies, chimeric antibodies, diabodies, linear antibodies, single chain antibodies, multispecific antibodies (e.g., bispecific antibodies), and modified configurations of the immunoglobulin molecule that comprise an antigen recognition site of the required specificity. Non-limiting examples of antibodies falling into the last category include glycosylation variants of antibodies, amino acid sequence variants of antibodies, and covalently modified antibodies. Additionally, a binding partner may be an antibody of any class, such as IgD, IgE, IgG, IgA, or IgM (or sub-class thereof, e.g., IgG1, IgG2, IgG3, IgG4, IgA1 and/or IgA2.

An antigen may be a molecule or a portion of a molecule that can have antibodies generated against it. Antigens may be peptides, polysaccharides and/or lipids. Some antigens may originate from within the body (a "self-antigen"), and some antigens may originate from the external environment (a "non-self-antigen").

In some embodiments, antibodies suitable for performing a chemical and/or biological reaction specifically bind to epitopes on their target molecules. An epitope (which may be referred to as an antigenic determinant) may be the part of the antigen recognized (or bound by) an antibody. For example, the epitope may be the specific piece of the antigen to which an antibody binds. The part of an antibody that binds to the epitope may be referred to as a paratope. An epitope may be a conformational epitope (composed of discontinuous amino acids or sections of the antigen) or a linear epitope (composed of continuous amino acids). Some proteins may share segments of high sequence homology and/or structural similarity. These similar proteins may have common epitopes (in other words, the epitopes on different antibodies may be bound by the same antibody). Further, a protein that has been processed differentially (such as a protein that has gone a further enzymatic process) may share some, but not all epitopes with its pre-processing form. Non-limiting examples of different epitopes that may be added or removed during processing include N-terminal signal peptides (as seen, for example, on pre-pro-peptides)

and changes seen when an inactive protein (e.g., a pro-peptide) is turned into an active form by post-translational modification.

When an antibody specifically binds to an epitope, it may engage in a binding reaction that is capable of discriminating between a target molecule and a non-target molecule. For example, a binding partner may specifically bind to a target molecule with greater than or equal to 2-fold greater affinity than to a non-target molecule with greater than or equal to 4-fold, greater than or equal to 5-fold, greater than or equal to 6-fold, greater than or equal to 7-fold, greater than or equal to 8-fold, greater than or equal to 9-fold, greater than or equal to 10-fold, greater than or equal to 20-fold, greater than or equal to 25-fold, greater than or equal to 50-fold, or greater than or equal to 100-fold greater affinity than to a non-target molecule.

The binding affinity of an antibody may be parametrized by its apparent association constant or $K_A$. The $K_A$ is the reciprocal of the dissociation constant ($K_D$). In some embodiments, a binding partner described herein has a binding affinity ($K_D$) of greater than or equal to $10^{-5}$ M, greater than or equal to $10^{-6}$ M, greater than or equal to $10^{-7}$ M, greater than or equal to $10^{-8}$ M, greater than or equal to $10^{-9}$ M, or greater than or equal to $10^{-10}$ M. An increased binding affinity corresponds to a decreased $K_D$. Higher affinity binding of a binding partner (e.g., an antibody) to a first molecule relative to a second molecule can be indicated by a higher $K_A$ (or a smaller numerical value $K_D$) for binding to the first target than the $K_A$ (or numerical value $K_D$) for binding to the second target. In such cases, the antibody has a specificity for the first molecule (e.g., a protein in a first conformation or mimic thereof) relative to the second molecule (e.g., the same protein in a second conformation or mimic thereof, or a second protein). Differences in binding affinity (e.g., specificity) can be greater than or equal to 1.5-fold, greater than or equal to 2-fold, greater than or equal to 3-fold, greater than or equal to 4-fold, greater than or equal to 5-fold, greater than or equal to 10-fold, greater than or equal to 15-fold, greater than or equal to 20-fold, greater than or equal to 37.5-fold, greater than or equal to 50-fold, greater than or equal to 70-fold, greater than or equal to 80-fold, greater than or equal to 90-fold, greater than or equal to 100-fold, greater than or equal to 500-fold, greater than or equal to 1000-fold, greater than or equal to 10,000-fold, greater than or equal to $10^5$-fold.

The binding of a target molecule (e.g., to detect the binding of a protein of interest, such as an antigen-bound antibody complex) may be quantified by interrogating an active molecule bound to a tracer antibody.

In some embodiments, labeled antibodies or antigen binding fragments may be used as tracers to detect antigen-bound antibody complexes. Examples of the types of labels which can be used to generate tracers include enzymes, radioisotopes, colloidal metals, fluorescent compounds, magnetic, chemiluminescent compounds, electrochemiluminescent groups, metal nanoparticles, and bioluminescent compounds. Radiolabeled antibodies may be prepared by coupling a radioactive isotope such as $^{153}$Eu, $^3$H, $^{32}$P, $^{35}$S, $^{59}$Fe, and/or $^{125}$I to the antibody or antigen binding fragment, which can then be detected by gamma counter, by a scintillation counter, and/or by autoradiography. In some embodiments, antibodies and antigen-binding fragments may be labeled with enzymes, such as yeast alcohol dehydrogenase, horseradish peroxidase, and/or alkaline phosphatase. After labelling, the antibody and/or antigen-binding fragment may be developed and detected spectrophotometrically and/or visually. Some labels may be used to react a chromogen into a detectable chromophore (e.g., if the chromogen is a precipitating dye).

Non-limiting examples of suitable fluorescent labels include fluorescein, fluorescein isothiocyanate, fluorescamine, rhodamine, Alexa Fluor® dyes (e.g., Alexa Fluor® 350, Alexa Fluor® 405, Alexa Fluor® 430, Alexa Fluor® 488, Alexa Fluor® 514, Alexa Fluor® 532, Alexa Fluor® 546, Alexa Fluor® 555, Alexa Fluor® 568, Alexa Fluor® 594, Alexa Fluor® 610, Alexa Fluor® 633, Alexa Fluor® 635, Alexa Fluor® 647, Alexa Fluor® 660, Alexa Fluor® 680, Alexa Fluor® 700, Alexa Fluor® 750, and/or Alexa Fluor® 790), and cyanine dyes (e.g., Cy2, Cy3, Cy3.5, Cy5, Cy5.5, Cy7, and/or Cy7.5). In some embodiments, labels also be time-resolved fluorescent (TRF) atoms (e.g., Eu and/or Sr with appropriate ligands to enhance TRF yield). More than one fluorophore capable of producing a fluorescence resonance energy transfer (FRET) may also be used. Non-limiting examples of suitable chemiluminescent labels include acridinium esters, luminol, imidazole, oxalate ester, and luciferin.

One non-limiting examples of a suitable electrochemiluminescent group is Ru.

In some embodiments, a label comprises a nanoparticle. Non-limiting examples of suitable nanoparticles include up-converting phosphorescent systems, nanodots, quantum dots, nanorods, and nanowires. The label linked to the antibody may also be a nucleic acid, which might then be amplified (e.g., using PCR) before quantification by one or more of optical, electrical or electrochemical means.

Some labels may be linked to a tracer. This linkage may comprise a covalent bond and/or a non-covalent bond.

In some embodiments, droplets in an array comprise one or more components suitable for facilitating a chemical and/or biological reaction. Such components may not be reactive themselves but may provide an environment that promotes the reaction. As one example, in some embodiments, droplets in an array comprise beads. For instance, each droplet may comprise a single bead and/or a portion of the droplets may each comprise a single bead. Reagents suitable for performing the reaction may be attached to the beads, but the beads themselves may not be reactive. In some embodiments, droplets may comprise beads on which a reaction may be performed. As an example, in some embodiments, droplets may comprise beads on which an assay (e.g., an ELISA assay) may be performed.

In some embodiments, a relatively high percentage of the droplets in an array of droplets have the same composition. For instance, greater than or equal to 75%, greater than or equal to 80%, greater than or equal to 85%, greater than or equal to 90%, greater than or equal to 95%, greater than or equal to 97.5%, greater than or equal to 99%, greater than or equal to 99.5%, greater than or equal to 99.9%, or 100% of the droplets in an array have the same composition. In some embodiments, less than or equal to 100%, less than or equal to 99.9%, less than or equal to 99.5%, less than or equal to 99%, less than or equal to 97.5%, less than or equal to 95%, less than or equal to 90%, less than or equal to 85%, or less than or equal to 80% of the droplets in an array have the same composition. Combinations of the above-referenced ranges are also possible (e.g., greater than or equal to 75% and less than or equal to 100%). Other ranges are also possible.

Droplets having the same composition may have the same chemical composition (e.g., they may comprise the same components in the same relative amounts). In some embodiments, an array of droplets comprises one species that may be present in some of the droplets but not others. In such embodiments, one, more, or all of the other species present in the droplets may be present in a relatively uniform amount across the droplets (e.g., an amount in one or more of the ranges above). By way of example, in some embodiments, an array of droplets may comprise some droplets that comprise a cell and some droplets that lack a cell. All of the droplets may comprise an otherwise-common set of components (e.g., any buffer and/or reagents) present in relatively uniform amounts with respect to each other.

In some embodiments, the composition of some or all of the droplets in an array of droplets changes over time. In such embodiments, it should be understood that the percentage of droplets having the same composition may be in one or more of the above-referenced ranges at one or more points in time (e.g., directly after deposition, before one or more experiments and/or manipulations have been performed on the array of droplets, before the array of droplets has been exposed to one or more stimuli). In some such embodiments, an array of droplets may have a percentage of droplets having the same composition in one or more of the ranges described above at some points in time but not at others (e.g., after one or more experiments and/or manipulations have been performed on the array of droplets, after the array of droplets has been exposed to one or more stimuli).

In the discussion elsewhere herein, it should be understood that, unless otherwise indicated, references to the properties of droplets in an array should be understood to refer to the properties of any particular droplet, to the properties of a majority of the droplets, and/or to the average properties of the droplets. For instance, unless otherwise indicated, references to droplet contents should be understood to mean that a single droplet in an array may comprise the specified contents, that the majority of the droplets in an array may comprise the specified contents, and/or that an average droplet in an array may comprise the specified contents. As another example, unless otherwise indicated, references to numerical properties of droplets (e.g., diameter, volume) should be understood to mean that a single droplet in an array may have the specified numerical property, that the majority of the droplets in an array may have the specified numerical property, and/or that the average numerical value of the property across all droplets is the specified value.

In some embodiments, a relatively large percentage of droplets in an array comprise cells. Without wishing to be bound by any particular theory, it is believed that it may be desirable for droplets to include single cells (e.g., for performing single cell assays) and/or a uniform number of cells (e.g., for performing consistent experiments in different droplets) but challenging to consistently produce such droplets. One approach for doing so is to interrogate each droplet prior to deposition and then to deposit the droplets comprising cells and dispose of the droplets lacking cells and/or comprising two or more cells. This approach has been described elsewhere herein, and may result in the formation of an array of droplets for which a relatively high number of the droplets comprise exactly one cell. For instance, greater than or equal to 90%, greater than or equal to 95%, greater than or equal to 98%, greater than or equal to 99%, greater than or equal to 99.5%, greater than or equal to 99.9%, greater than or equal to 99.95%, greater than or equal to 99.99%, or 100% of the droplets in the array may comprise exactly one cell. In some embodiments, less than or equal to 100%, less than or equal to 99.99%, less than or equal to 99.95%, less than or equal to 99.9%, less than or equal to 99.5%, or less than or equal to 99% of the droplets in the array comprise exactly one cell. Combinations of the above-referenced ranges are also possible (e.g., greater than or equal to 90% and less than or equal to 100%, or greater than or equal to 98% and less than or equal to 100%). Other ranges are also possible.

Another approach for consistently producing droplets comprising exactly one cell is to form droplets from a fluid comprising a relatively low number of cells. The droplets produced from such a fluid may have a number of cells that is determined by the Poisson distribution. When the fluid is fairly dilute in cells, the Poisson distribution will result in the majority of the droplets comprising exactly zero cells, a low amount of droplets comprising exactly one cell, and even lower amounts of droplets comprising two or more cells. In such embodiments, the percentage of droplets comprising exactly one cell may be less than or equal to 10%, less than or equal to 7.5%, less than or equal to 5%, less than or equal to 2%, less than or equal to 1%, less than or equal to 0.75%, less than or equal to 0.5%, or less than or equal to 0.2%. In such embodiments, the percentage of droplets comprising exactly one cell may be greater than or equal to 0.1%, greater than or equal to 0.2%, greater than or equal to 0.5%, greater than or equal to 0.75%, greater than or equal to 1%, greater than or equal to 2%, greater than or equal to 5%, or greater than or equal to 7.5%. Combinations of the above-referenced ranges are also possible (e.g., less than or equal to 10% and greater than or equal to 0.1%). Other ranges are also possible.

It should also be noted that it may be possible for an array to comprise an amount of droplets having an amount of cells in one or more of the ranges described in the preceding paragraphs that is formed from a procedure other than those described in those paragraphs.

In some embodiments, an array of droplets comprises droplets comprising a coating. The coating may coat the external surfaces of the droplets (e.g., at the air/liquid interface), which may affect the surface tension of the droplet. In some embodiments, one, some, or all of the materials forming the coating of the droplet do not diffuse into the interior of the droplet. Advantageously, this may facilitate the formation of coatings on droplets comprising one or more materials that would not be desirable for inclusion in the interiors of the droplets. As an example, in some embodiments, the interior of a droplet may comprise a cell and a coating may comprise a species toxic to the cell. If the coating is maintained on the outside of the droplet (e.g., by being immiscible with the droplet interior), then the cell in the interior of the droplet may be unaffected (or minimally affected) by the coating. In some embodiments, a droplet coating comprises a hydrophobic substance such as an oil, e.g., a mineral oil or a fluorinated oil.

Droplets in an array may be a variety of suitable sizes. In some embodiments, an array comprises droplets having a diameter of greater than or equal to 15 microns, greater than or equal to 20 microns, greater than or equal to 25 microns, greater than or equal to 30 microns, greater than or equal to 40 microns, greater than or equal to 50 microns, greater than or equal to 75 microns, greater than or equal to 100 microns, greater than or equal to 125 microns, greater than or equal to 150 microns, greater than or equal to 175 microns, greater than or equal to 200 microns, or greater than or equal to 225 microns. In some embodiments, an array comprises droplets having a diameter of less than or equal to 250 microns, less than or equal to 200 microns, less than or equal to 175 microns, less than or equal to 150 microns, less than or equal to 125 microns, less than or equal to 100 microns, less than or equal to 75 microns, less than or equal to 50 microns, less than or equal to 40 microns, less than or equal to 30 microns, less than or equal to 25 microns, or less than or equal to 20 microns. Combinations of the above-referenced ranges are also possible (e.g., greater than or equal to 15 microns and less than or equal to 250 microns). Other ranges are also possible.

The volume of the droplets in an array may generally be selected as desired. In some embodiments, an array comprises droplets having a volume of greater than or equal to 20 pL, greater than or equal to 50 pL, greater than or equal to 75 pL, greater than or equal to 100 pL, greater than or equal to 200 pL, greater than or equal to 500 pL, greater than or equal to 750 pL, greater than or equal to 1 nL, greater than or equal to 2 nL, greater than or equal to 5 nL, greater than or equal to 7.5 nL, greater than or equal to 10 nL, greater than or equal to 20 nL, greater than or equal to 50 nL, or greater than or equal to 75 nL. In some embodiments, an array comprises droplets having an average volume of less than or equal to 100 nL, less than or equal to 50 nL, less than or equal to 20 nL, less than or equal to 10 nL, less than or equal to 7.5 nL, less than or equal to 5 nL, less than or equal to 2 nL, less than or equal to 1 nL, less than or equal to 750 pL, less than or equal to 500 pL, less than or equal to 200 pL, less than or equal to 100 pL, less than or equal to 75 pL, or less than or equal to 50 pL. Combinations of the above-referenced ranges are also possible (e.g., greater than or equal to 20 pL and less than or equal to 100 nL). Other ranges are also possible.

In some embodiments, an array comprises droplets that are relatively monodisperse (e.g., with respect to diameter and/or volume). For instance, an array may comprise droplets for which the coefficient of variation for the diameter and/or the volume of the droplets is less than or equal to 10%, less than or equal to 7.5%, less than or equal to 5%, less than or equal to 2.5%, less than or equal to 1%, or less than or equal to 0.75%. An array may comprise droplets for which the coefficient of variation for the diameter and/or volume of the droplets is greater than or equal to 0.5%, greater than or equal to 0.75%, greater than or equal to 1%, greater than or equal to 2.5%, greater than or equal to 5%, or greater than or equal to 7.5%. Combinations of the above-referenced ranges are also possible (e.g., less than or equal to 10% and greater than or equal to 0.5%, or less than or equal to 5% and greater than or equal to 0.5%). Other ranges are also possible.

Arrays of droplets may comprise a variety of suitable amounts of droplets. In some embodiments, an array of droplets comprises greater than or equal to 10 droplets, greater than or equal to 20 droplets, greater than or equal to 50 droplets, greater than or equal to 75 droplets, greater than or equal to 100 droplets, greater than or equal to 200 droplets, greater than or equal to 500 droplets, greater than or equal to 750 droplets, greater than or equal to 1000 droplets, greater than or equal to 2000 droplets, greater than or equal to 5000 droplets, greater than or equal to 7500 droplets, greater than or equal to 10000 droplets, greater than or equal to 20000 droplets, greater than or equal to 50000 droplets, or greater than or equal to 75000 droplets. In some embodiments, an array of droplets comprises less than or equal to 100000 droplets, less than or equal to 75000 droplets, less than or equal to 50000 droplets, less than or equal to 20000 droplets, less than or equal to 10000 droplets, less than or equal to 7500 droplets, less than or equal to 5000 droplets, less than or equal to 2000 droplets, less than or equal to 1000 droplets, less than or equal to 750 droplets, less than or equal to 500 droplets, less than or equal to 200 droplets, less than or equal to 100 droplets, less than or equal to 75 droplets, less than or equal to 50 droplets, or less than or equal to 20 droplets. Combinations of the above-referenced ranges are also possible (e.g., greater than or equal to 10 droplets and less than or equal to 100000 droplets). Other ranges are also possible.

Arrays of droplets may be arranged on a surface at a variety of suitable areal densities. In some embodiments, droplets are positioned on a surface at a density of greater than or equal to 1 droplet per square millimeter, greater than or equal to 2 droplets per square millimeter, greater than or equal to 5 droplets per square millimeter, greater than or equal to 7.5 droplets per square millimeter, greater than or equal to 10 droplets per square millimeter, greater than or equal to 15 droplets per square millimeter, greater than or equal to 20 droplets per square millimeter, greater than or equal to 25 droplets per square millimeter, greater than or equal to 30 droplets per square millimeter, greater than or equal to 35 droplets per square millimeter, greater than or equal to 40 droplets per square millimeter, greater than or equal to 50 droplets per square millimeter, greater than or equal to 60 droplets per square millimeter, greater than or equal to 70 droplets per square millimeter, greater than or equal to 80 droplets per square millimeter, or greater than or equal to 90 droplets per square millimeter. In some embodiments, droplets are positioned on a surface at a density of less than or equal to 100 droplets per square millimeter, less than or equal to 90 droplets per square millimeter, less than or equal to 80 droplets per square millimeter, less than or equal to 70 droplets per square millimeter, less than or equal to 60 droplets per square millimeter, less than or equal to 50 droplets per square millimeter, less than or equal to 40 droplets per square millimeter, less than or equal to 35 droplets per square millimeter, less than or equal to 30 droplets per square millimeter, less than or equal to 25 droplets per square millimeter, less than or equal to 20 droplets per square millimeter, less than or equal to 15 droplets per square millimeter, less than or equal to 10 droplets per square millimeter, less than or equal to 7.5 droplets per square millimeter, less than or equal to 5 droplets per square millimeter, or less than or equal to 2 droplets per square millimeter. Combinations of the above-referenced ranges are also possible (e.g., greater than or equal to 1 droplet per square millimeter and less than or equal to 100 droplets per square millimeter). Other ranges are also possible.

A variety of surfaces may be employed to support the arrays of droplets described herein. In some embodiments, the surface is a surface of a substrate (e.g., an upper surface of a substrate). It is also possible for the surface to be a surface of a coating disposed on a substrate (e.g., an upper surface of a coating disposed on a substrate). For instance, the surface may be a surface of a thin film disposed on a substrate and/or a surface of a self-assembled monolayer disposed on a substrate. When present, the coatings may be covalently bonded to the surface of the substrate or non-covalently bonded to the surface of the substrate. Non-limiting examples of suitable substrates include substrates comprising glass (e.g., glass slides) and substrates comprising plastic (e.g., cyclo olefin polymers, polymethyl methacrylate, polycarbonate, polyethylene, polypropylene, and polystyrene). Non-limiting examples of suitable coatings include coatings comprising crystalline, semicrystalline, and/or amorphous fluorinated polymers (e.g., polytetrafluoroethylene, also referred to as Teflon, CYTOP®), fluorinated small molecules, fluorinated oligomers, silanes (e.g., octadecyltrichlorosilane, also referred to as ODTS, and fluorosilanes), and bromo-terminated molecules (e.g., bromo-terminated alkanes).

As described elsewhere herein, in some embodiments, a surface on which an array of droplets is disposed is relatively hydrophobic. In some embodiments, such a surface has a water contact angle of greater than or equal to 90°, greater than or equal to 95°, greater than or equal to 100°, greater than or equal to 105°, greater than or equal to 110°, greater than or equal to 115°, greater than or equal to 120°, greater than or equal to 125°, greater than or equal to 130°, greater than or equal to 135°, greater than or equal to 140°, greater than or equal to 145°, greater than or equal to 150°, greater than or equal to 155°, greater than or equal to 160°, or greater than or equal to 165°. In some embodiments, such a surface has a water contact angle of less than or equal to 170°, less than or equal to 165°, less than or equal to 160°, less than or equal to 155°, less than or equal to 150°, less than or equal to 145°, less than or equal to 140°, less than or equal to 135°, less than or equal to 130°, less than or equal to 125°, less than or equal to 120°, less than or equal to 115°, less than or equal to 110°, less than or equal to 105°, less than or equal to 100°, or less than or equal to 95°. Combinations of the above-referenced ranges are also possible (e.g., greater than or equal to 90° and less than or equal to 170°. Other ranges are also possible. The water contact angle may be determined in accordance with ASTM D7334-08 (2013).

In some embodiments, a substrate, and/or any coating disposed thereon, comprising a surface on which an array of droplets is disposed is relatively transparent at one or more wavelengths. For instance, in some embodiments, the substrate and/or coating has a high transparency at wavelengths of greater than or equal to 200 nm, greater than or equal to 250 nm, greater than or equal to 300 nm, greater than or equal to 350 nm, greater than or equal to 400 nm, greater than or equal to 450 nm, greater than or equal to 500 nm, greater than or equal to 550 nm, greater than or equal to 600 nm, greater than or equal to 650 nm, greater than or equal to 700 nm, greater than or equal to 750 nm, greater than or equal to 800 nm, greater than or equal to 850 nm, greater than or equal to 900 nm, or greater than or equal to 950 nm. In some embodiments, the substrate and/or coating has a high transparency at wavelengths of less than or equal to 1000 nm, less than or equal to 950 nm, less than or equal to 900 nm, less than or equal to 850 nm, less than or equal to 800 nm, less than or equal to 750 nm, less than or equal to 700 nm, less than or equal to 650 nm, less than or equal to 600 nm, less than or equal to 550 nm, less than or equal to 500 nm, less than or equal to 450 nm, less than or equal to 400 nm, less than or equal to 350 nm, less than or equal to 300 nm, or less than or equal to 250 nm. Combinations of the above-referenced ranges are also possible (e.g., greater than or equal to 200 nm and less than or equal to 1000 nm). Other ranges are also possible.

The transmittance of the substrate at wavelengths in one or more of the ranges described in the preceding paragraph may be appreciable. For instance, in some embodiments, a substrate has a transmittance at wavelengths in one or more of the ranges described in the preceding paragraph of greater than or equal to 85%, greater than or equal to 90%, greater than or equal to 95%, greater than or equal to 97.5%, greater than or equal to 99%, greater than or equal to 99.5%, or greater than or equal to 99.9%. In some embodiments, a substrate has a transmittance at wavelengths in one or more of the ranges described in the preceding paragraph of less than or equal to 100%, less than or equal to 99.9%, less than or equal to 99.5%, less than or equal to 99%, less than or equal to 97.5%, less than or equal to 95%, or less than or equal to 90%. Combinations of the above-referenced ranges are also possible (e.g., greater than or equal to 85% and less than or equal to 100%). Other ranges are also possible. The transmittance may be determined in accordance with ASTM D1746-15.

The substrates described herein may have a variety of suitable sizes. In some embodiments, a substrate has a dimension of greater than or equal to 1 cm, greater than or equal to 2 cm, greater than or equal to 5 cm, greater than or equal to 7.5 cm, greater than or equal to 10 cm, greater than or equal to 12.5 cm, greater than or equal to 15 cm, or greater than or equal to 17.5 cm. In some embodiments, a substrate has a dimension of less than or equal to 20 cm, less than or equal to 17.5 cm, less than or equal to 15 cm, less than or equal to 12.5 cm, less than or equal to 10 cm, less than or equal to 7.5 cm, less than or equal to 5 cm, or less than or equal to 2 cm. Combinations of the above-referenced ranges are also possible (e.g., greater than or equal to 1 cm and less than or equal to 20 cm). Other ranges are also possible.

The ranges in the preceding paragraph may refer to any suitable dimension of the substrate. For instance, in some embodiments, a substrate has a length in one or more of the above-referenced ranges, a width in one or more of the above-referenced ranges, a longest dimension in one or more of the above-referenced ranges, and/or a shortest dimension in one or more of the above-referenced ranges.

The substrates described herein may have a variety of suitable thicknesses. In some embodiments, a substrate has a thickness of less than or equal to 2 mm, less than or equal to 1.75 mm, less than or equal to 1.5 mm, less than or equal to 1.25 mm, less than or equal to 1 mm, less than or equal to 0.75 mm, less than or equal to 0.5 mm, or less than or equal to 0.2 mm. In some embodiments, a substrate has a thickness of greater than or equal to 0.1 mm, greater than or equal to 0.2 mm, greater than or equal to 0.5 mm, greater than or equal to 0.75 mm, greater than or equal to 1 mm, greater than or equal to 1.25 mm, greater than or equal to 1.5 mm, or greater than or equal to 1.75 mm. Combinations of the above-referenced ranges are also possible (e.g., less than or equal to 2 mm and greater than or equal to 0.1 mm). Other ranges are also possible.

The substrates described herein may have a variety of suitable surface areas. In some embodiments, a substrate has a surface area of greater than or equal to 1 cm$^2$, greater than or equal to 2 cm$^2$, greater than or equal to 5 cm$^2$, greater than or equal to 7.5 cm$^2$, greater than or equal to 10 cm$^2$, greater than or equal to 20 cm$^2$, greater than or equal to 50 cm$^2$, greater than or equal to 75 cm$^2$, greater than or equal to 100 cm$^2$, greater than or equal to 150 cm$^2$, greater than or equal to 200 cm$^2$, greater than or equal to 250 cm$^2$, greater than or equal to 300 cm$^2$, or greater than or equal to 350 cm$^2$. In some embodiments, a substrate has a surface area of less than or equal to 400 cm$^2$, less than or equal to 350 cm$^2$, less than or equal to 300 cm$^2$, less than or equal to 250 cm$^2$, less than or equal to 200 cm$^2$, less than or equal to 150 cm$^2$, less than or equal to 100 cm$^2$, less than or equal to 75 cm$^2$, less than or equal to 50 cm$^2$, less than or equal to 20 cm$^2$, less than or equal to 10 cm$^2$, less than or equal to 7.5 cm$^2$, less than or equal to 5 cm$^2$, or less than or equal to 2 cm$^2$. Combinations of the above-referenced ranges are also possible (e.g., greater than or equal to 1 cm$^2$ and less than or equal to 400 cm$^2$). Other ranges are also possible.

The surface areas described in the preceding paragraph may refer to the surface areas of the substrate as a whole (e.g., including both portions that include the array of droplets and portions that lack the array of droplets, including both portions of the substrate that are flat and portions of the surface that are not flat, including both portions of the substrate that have a uniform and hydrophobic surface chemistry and those that have a different surface chemistry from the portions having the uniform and hydrophobic surface chemistry). In other words, in some embodiments, a substrate as a whole has a surface area in one or more of the ranges in the preceding paragraph. It is also possible for a substrate to comprise a portion having a surface area in one or more ranges described in the preceding paragraph (e.g., a portion including an array of droplets, a portion comprising a surface that is flat and has a uniform and hydrophobic surface chemistry). In the latter case, the substrate as a whole may (or may not) have a surface area outside of the ranges described above.

As described elsewhere herein, some embodiments relate to droplets enclosed by an enclosure. When present, the enclosure may enclose a volume. That volume may have a thickness (e.g., extending in a dimension perpendicular from/to a surface supporting the enclosed droplets) and an area (e.g., an area of a surface enclosed by the enclosure that supports the enclosed droplets). The thickness of the enclosed volume may be selected as desired. In some embodiments, the enclosed volume has a thickness of greater than or equal to 0.1 mm, greater than or equal to 0.2 mm, greater than or equal to 0.5 mm, greater than or equal to 0.75 mm, greater than or equal to 1 mm, greater than or equal to 1.5 mm, greater than or equal to 2 mm, greater than or equal to 2.5 mm, greater than or equal to 3 mm, greater than or equal to 3.5 mm, greater than or equal to 4 mm, or greater than or equal to 4.5 mm. In some embodiments, the enclosed volume has a thickness of less than or equal to 5 mm, less than or equal to 4.5 mm, less than or equal to 4 mm, less than or equal to 3.5 mm, less than or equal to 3 mm, less than or equal to 2.5 mm, less than or equal to 2 mm, less than or equal to 1.5 mm, less than or equal to 1 mm, less than or equal to 0.75 mm, less than or equal to 0.5 mm, or less than or equal to 0.2 mm. Combinations of the above-referenced ranges are also possible (e.g., greater than or equal to 0.1 mm and less than or equal to 5 mm). Other ranges are also possible.

The area of an enclosed volume may also be selected as desired. In some embodiments, an enclosed volume has an area of greater than or equal to 1 cm$^2$, greater than or equal to 2 cm$^2$, greater than or equal to 5 cm$^2$, greater than or equal to 7.5 cm$^2$, greater than or equal to 10 cm$^2$, greater than or equal to 20 cm$^2$, greater than or equal to 50 cm$^2$, greater than or equal to 75 cm$^2$, greater than or equal to 100 cm$^2$, greater than or equal to 150 cm$^2$, greater than or equal to 200 cm$^2$, greater than or equal to 250 cm$^2$, greater than or equal to 300 cm$^2$, or greater than or equal to 350 cm$^2$. In some embodiments, an enclosed volume has an area of less than or equal to 400 cm$^2$, less than or equal to 350 cm$^2$, less than or equal to 300 cm$^2$, less than or equal to 250 cm$^2$, less than or equal to 200 cm$^2$, less than or equal to 150 cm$^2$, less than or equal to 100 cm$^2$, less than or equal to 75 cm$^2$, less than or equal to 50 cm$^2$, less than or equal to 20 cm$^2$, less than or equal to 10 cm$^2$, less than or equal to 7.5 cm$^2$, less than or equal to 5 cm$^2$, or less than or equal to 2 cm$^2$. Combinations of the above-referenced ranges are also possible (e.g., greater than or equal to 1 cm$^2$ and less than or equal to 400 cm$^2$). Other ranges are also possible.

When present, an enclosure may enclose a variety of suitable numbers of droplets. In some embodiments, an enclosure encloses greater than or equal to 5 droplets, greater than or equal to 10 droplets, greater than or equal to 20 droplets, greater than or equal to 50 droplets, greater than or equal to 75 droplets, greater than or equal to 100 droplets, greater than or equal to 200 droplets, greater than or equal to 500 droplets, greater than or equal to 750 droplets, greater than or equal to 1000 droplets, greater than or equal to 2000 droplets, greater than or equal to 5000 droplets, greater than or equal to 7500 droplets, greater than or equal to 10000 droplets, greater than or equal to 20000 droplets, greater than or equal to 50000 droplets, or greater than or equal to 75000 droplets. In some embodiments, an enclosure encloses less than or equal to 100000 droplets, less than or equal to 75000 droplets, less than or equal to 50000 droplets, less than or equal to 20000 droplets, less than or equal to 10000 droplets, less than or equal to 7500 droplets, less than or equal to 5000 droplets, less than or equal to 2000 droplets, less than or equal to 1000 droplets, less than or equal to 750 droplets, less than or equal to 500 droplets, less than or equal to 200 droplets, less than or equal to 100 droplets, less than or equal to 75 droplets, less than or equal to 50 droplets, less than or equal to 20 droplets, or less than or equal to 10 droplets. Combinations of the above-referenced ranges are also possible (e.g., greater than or equal to 5 droplets and less than or equal to 100000 droplets). Other ranges are also possible.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of forming an array of droplets, comprising:
   depositing a plurality of droplets onto a surface; and
   enclosing some or all of the droplets in the plurality of droplets in an enclosure, wherein:
      the surface is flat;
      the surface has a uniform surface chemistry;

23 the surface is hydrophobic;

the plurality of droplets comprises greater than or equal to 10 droplets;

the enclosure reduces and/or prevents evaporation of water from the droplets; and the density of the droplets on the surface is greater than or equal to 1 droplet per square millimeter of the surface.

2. A method as in claim 1, wherein at least a portion of the droplets comprise a single cell.

3. A method as in claim 1, wherein, prior to deposition, each droplet is interrogated to determine whether or not it comprises a cell.

4. A method as in claim 3, further comprising disposing of any droplets lacking cells and/or comprising two or more cells.

5. A method as in claim 1, wherein the droplets comprise water.

6. A method as in claim 1, wherein the droplets comprise a coating.

7. A method as in claim 6, wherein the coating comprises an oil.

8. A method as in claim 1, wherein at least a portion of the droplets comprise a bead.

9. A method as in claim 1, wherein the surface is an upper surface of a substrate, of a thin film disposed on a substrate, and/or of a self-assembled monolayer disposed on a substrate.

10. A method as in claim 9, wherein the substrate is transparent.

11. A method as in claim 9, wherein the substrate further comprises a water reservoir.

12. A method as in claim 11, wherein the water reservoir takes the form of a depression in the substrate.

13. A method as in claim 11, wherein a raised ridge is positioned between the water reservoir and the surface.

14. A method as in claim 1, further comprising performing a single cell assay on at least a portion of the droplets.

15. A method as in claim 1, further comprising growing cells in at least a portion of the plurality of droplets.

16. A method as in claim 1, wherein the enclosure comprises a top surface.

17. A method as in claim 16, wherein the top surface is hydrophobic.

18. A method as in claim 16, wherein for each of the plurality of droplets, at least a portion of droplet is in contact with the top surface.

19. A method as in claim 1, further comprising performing FRET on the droplets.

20. An article, comprising:

a plurality of droplets;

a surface; and an enclosure, wherein:

the droplets in the plurality of droplets are disposed on the surface;

the surface is flat;

the surface has a uniform surface chemistry;

the surface is hydrophobic;

the plurality of droplets comprises greater than or equal to 10 droplets;

some or all of the droplets in the plurality of droplets are enclosed by an enclosure;

the enclosure reduces and/or prevents evaporation of water from the droplets; and the density of the droplets on the surface is greater than or equal to 1 droplet per square millimeter of the surface.

* * * * *